United States Patent
Lauk et al.

(10) Patent No.: US 7,661,426 B2
(45) Date of Patent: Feb. 16, 2010

(54) METHOD FOR CONTROLLING THE PRESSURE SUPPLIED BY A CPAP DEVICE, CPAP DEVICE AND STORAGE MEDIUM

(76) Inventors: Michael Lauk, IM Wannele 11, Freiburg (DE) 79111; Siegfried Häussler, I.-Drewitz-Allee 43, Freiburg (DE) 79111; Mirko Wagner, Hertzal 121, Oberkirch-Nussbach (DE) 77704

( * ) Notice: Subject to any disclaimer, the term of this patent is extended or adjusted under 35 U.S.C. 154(b) by 542 days.

(21) Appl. No.: 11/132,462

(22) Filed: May 19, 2005

(65) Prior Publication Data

US 2005/0211248 A1    Sep. 29, 2005

Related U.S. Application Data

(63) Continuation of application No. PCT/DE03/03610, filed on Oct. 30, 2003.

(30) Foreign Application Priority Data

Nov. 19, 2002   (DE) ................ 102 53 935

(51) Int. Cl.
*A61M 11/00* (2006.01)
(52) U.S. Cl. .............. 128/204.18; 128/204.23
(58) Field of Classification Search ........... 128/200.24, 128/204.18, 204.21, 204.23; 600/538
See application file for complete search history.

(56) References Cited

U.S. PATENT DOCUMENTS

| | | | | |
|---|---|---|---|---|
| 5,199,424 A | * | 4/1993 | Sullivan et al. | 128/204.18 |
| 5,335,654 A | | 8/1994 | Rapoport | |
| 5,458,137 A | * | 10/1995 | Axe et al. | 128/204.23 |
| 5,537,997 A | * | 7/1996 | Mechlenburg et al. | 128/204.23 |
| 5,582,163 A | * | 12/1996 | Bonassa | 128/204.26 |
| 5,645,054 A | * | 7/1997 | Cotner et al. | 128/204.23 |
| 5,704,345 A | * | 1/1998 | Berthon-Jones | 128/204.23 |
| 5,740,795 A | | 4/1998 | Brydon | |
| 5,865,173 A | * | 2/1999 | Froehlich | 128/204.23 |
| 6,041,780 A | * | 3/2000 | Richard et al. | 128/204.18 |

(Continued)

FOREIGN PATENT DOCUMENTS

DE   198 49 571   5/2000

(Continued)

OTHER PUBLICATIONS

Avram R. Gold, MD; Alan R. Schwartz, MD, "The Pharyngeal Critical Pressure*," Chest/110/4, Oct. 1996, pp. 1077-1088.

(Continued)

*Primary Examiner*—Steven O Douglas
(74) *Attorney, Agent, or Firm*—King & Schickli, PLLC (57) ABSTRACT

The present invention relates to a method for controlling the pressure supplied by a CPAP device. The method comprises repeated measurement of a respiratory air flow during operation of the device and determining at least one respiratory event from the measured time-dependent behavior of the respiratory flow, the respiratory event representing an indication that the pressure supplied by the CPAP device is too low. Furthermore, the method comprises a slow, quasi ramp-like lowering of the pressure supplied by the CPAP device as long as no respiratory event is detected. Furthermore, the invention relates to a CPAP device for carrying out such a method and to a storage medium with a corresponding program.

14 Claims, 2 Drawing Sheets

U.S. PATENT DOCUMENTS

| | | | |
|---|---|---|---|
| 6,530,372 B1 * | 3/2003 | Madaus et al. | 128/204.23 |
| 6,622,726 B1 * | 9/2003 | Du | 128/204.26 |
| 7,089,936 B2 | 8/2006 | Madaus et al. | |
| 2002/0185131 A1 | 12/2002 | Madaus et al. | |

FOREIGN PATENT DOCUMENTS

| | | |
|---|---|---|
| DE | 691 32 030 | 10/2000 |
| DE | 101 18 968 | 10/2002 |
| EP | 0 934 723 | 8/1999 |
| EP | 0 612 257 | 6/2000 |
| WO | WO 94/23780 | 10/1994 |
| WO | WO 99/24099 | 5/1999 |
| WO | WO 00/24446 | 5/2000 |

OTHER PUBLICATIONS

Alan R. Schwartz; James A. Rowley; David C. Thut; Solbert Permutt; Philip L. Smith, "Structural Basis for Alterations in Upper Airway Collapsibility," Sleep, 19(10), pp. S184-S188.

* cited by examiner

METHOD FOR CONTROLLING THE PRESSURE SUPPLIED BY A CPAP DEVICE, CPAP DEVICE AND STORAGE MEDIUM

CROSS REFERENCE TO RELATED CO-PENDING APPLICATIONS

This application is a continuation of international PCT application number PCT/DE2003/03610 filed on Oct. 30, 2003 and entitled METHOD FOR CONTROLLING THE PRESSURE PROVIDED BY A CPAP DEVICE, CPAP DEVICED AND STORAGE MEDIUM and German patent application number 102 53 935.9 filed on Nov. 19, 2002 and entitled VERFAHREN ZUM STEUERN DES VON EINEM CPAP-GERÄT GELIEFERTEN DRUCKS, CPAP-GERÄT SOWIE SPEICHERMEDIUM the contents of which are expressly incorporated herein by reference.

FIELD OF THE INVENTION

The present invention relates to a method for controlling the pressure supplied by a CPAP device, a CPAP device for carrying out such a method, and a corresponding storage medium. The present invention particularly relates to a method in which the pressure is adjusted in dependence upon respiratory events which represent an indication that the pressure supplied by the CPAP device is too low.

BACKGROUND OF THE INVENTION

Known are devices for carrying out CPAP (continuous positive airway pressure) therapy. The CPAP therapy is described in Chest. Volume No. 110, pages 1077-1088, October 1996 und in Sleep, Volume No. 19, pages 184-188. A CPAP device applies a positive overpressure of up to approximately 30 mbar into the patient's respiratory airway by means of a compressor, preferably via a humidifier, via a hose and a nose mask. Said overpressure is to ensure that the upper respiratory airway remains fully opened for the whole night, so that no obstructive breathing disorders (apneas) will occur (DE 198 49 571 A1).

Figure 1:
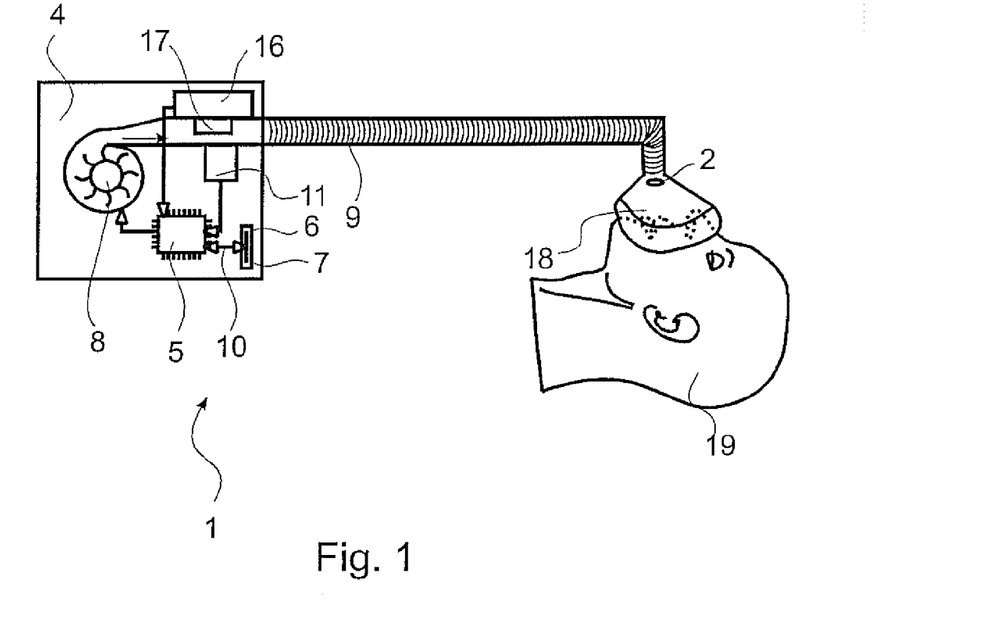
FIG. 1 shows a CPAP device.

FIG. 1 shows a CPAP device 1 and a patient 19. The CPAP device, in turn, comprises a compressor 4, a respiration tube 9, a respiration mask 18, a pressure sensor 11 and a flow sensor 16. For generating an overpressure the compressor contains a turbine 8. The turbine is also designated as a fan, fan unit, compressor, ventilator, or blower. These terms are used as synonyms in this patent. In the illustrated CPAP device, the pressure sensor 11 is positioned in the compressor casing and measures the pressure generated by the turbine. The pressure measuring device may be connected via a flexible tube to the respiration mask, thereby measuring the pressure in the respiration mask. Finally, the pressure sensor may also be located in the respiration mask and connected to the compressor casing via electrical lines. In or near the mask, one or several small holes 2 are provided, resulting in an air flow from the compressor to the holes 2 on time average. This prevents enrichment of $CO_2$ in the respiration tube 9, so that the patient can be supplied with oxygen.

The rotational speed of the turbine 8 is controlled by a microcontroller 5 such that the actual pressure measured with the pressure sensor 11 corresponds to a predetermined desired pressure. The desired pressure is normally preset under the supervision of a physician and is designated as titration pressure. The flow sensor may e.g. be a sensor with a heating wire 17. In another constructional form of the CPAP device, a constriction may be provided in the respiration tube for respiratory flow measurement, the differential pressure being measured via the constriction. The pressure sensors may directly be arranged in the respiration tube or connected to said tube via further pressure measurement tubes. The microcontroller 5 may also take over pressure control.

It was found that the overpressure produced by the CPAP device was considered by patients as an unpleasant resistance against which they had to exhale. That is why control methods were developed for CPAP devices for lowering the desired pressure as much as possible. Such a control is known from WO00/24446. Such a control is based on an algorithm in the case of which at least three pressure values are successively set during an "AutoSet" operation. In cases where the breath volume is independent of the set pressures, the pressures have been too high. When the breath volume increases with the set pressures, the pressures have been too low.

To reduce the overpressure considered to be unpleasant, BiPAP devices and multilevel devices have also been developed. Such a device is described in DE 691 32 030 T2. The pressure is raised through a valve during inhalation and lowered during exhalation. The valve is controlled such that the pressure is kept constant during inhalation and during exhalation. When the valve position is changed only slowly during an inhalation process, this is interpreted as the end of the inhalation process. Inaudible vibrations or pressure changes can be evaluated to determine whether the patient's breathing is regular, irregular or apneic. Moreover, the duration of inhalation and exhalation as well as the flow velocities can be determined. Such information can be stored in a memory. Finally, it is possible to calculate an admittance of respiratory flow divided by pressure. The time-dependent behavior of the admittance can be compared with the stored admittance schemes. The number of the best fitting admittance scheme can be used as an "indicator" for a table which contains the action to be performed, such as an increase in pressure.

WO 94/23780 describes a method for controlling the pressure of a CPAP device. In the absence of breathing disorders during sleep the pressure is reduced gradually. In the presence of sleep disorders, such as apneas, hypopneas or snoring, the pressure is increased. U.S. Pat. No. 5,335,654 and EP 0 934 723 A1 describe a similar method.

EP 0 612 257 B1 also describes an auto CPAP system which detects apneas, hypopneas and unstable breathing to set the pressure.

WO 99/24099 describes a control method for an auto CPAP device which takes into account apneas, hypopneas, reduced respiratory flow and snoring.

According to U.S. Pat. No. 5,740,795 the respiratory flow signal is supplied to a band-limited differentiator. When the output signal of the differentiator exceeds an inhalation threshold or when an exhalation threshold is not reached, an exhalation detection signal or an inhalation detection signal, respectively, is determined.

EP 0 934 723 A1 also refers to the control of a CPAP device on the basis of the detection of apneas and partial occlusion of the upper airway.

Furthermore, DE 101 18 968 describes a control method for CPAP device. DE 101 18 968 is included by reference in this application. The control method first calculates features from a measured respiratory flow curve and a measured actual pressure curve of a CPAP device. Special combinations of the features are combined to form detectors. In the detectors, flags are set when they detect an event, i.e., when they are responsive to the event. The control method will then change the desired pressure on the basis of the event flags of the detectors. The control method includes three different states, namely a normal state, a sensitive state and a leakage state, which can be switched to and fro. Some detectors operate in the sensitive state with parameters differing from the normal state. In the sensitive state, the control method changes when the control method reduces pressure in the normal state. Thanks to the selection of the parameters for the sensitive state the control method will react faster if the actual CPAP pressure is too low. For instance, when the mask is removed, the control will change into the leakage state.

The features comprise the expiration time, a reverse correlation, a mean inspiration volume, a mean curvature of the respiratory flow during inspiration and the frequency of zero passages in the changing portion of the actual CPAP pressure.

During transition from inspiration to expiration a pronounced flank can be detected in the respiratory flow, said flank being used for detecting individual breaths. The local maxima of the first derivative correspond to the maximum increase in the respiratory flow during transition between inspiration and expiration. From the end of the inspiration the beginning of the inspiration is looked for by searching for the first local minimum in the derivative. The expiration time is obtained as the time difference between a minimum of the derivative and the maximum located before the minimum.

For calculating the reverse correlation the most recent breath is compared with preceding breaths by calculating a cross correlation function. The cross correlation function has values between one and minus one, the correlation being equal to one when the two breaths fit each other exactly, and it becomes equal minus one when the curves correlate with one another in a negative way, i.e. when a peak in the respiratory pattern exactly corresponds to a valley in the data piece considered. The mean value over a specific number of local maxima of the cross correlation function before the actual point of time is designated as reverse correlation.

For calculating the mean curvature of the respiratory flow during inspiration the first derivative of the respiratory flow after time is estimated or calculated during inspiration. Subsequently, a straight line is adapted to the first derivative. The slope of this adapted straight line gives the mean curvature of the inspiration.

It has been found that the number of zero passages in the changing portion of the actual CPAP pressure is a reliable feature for snoring, for the pressure regulation of a typical CPAP device is not so fast that it would be capable of correcting snoring noise as well. The zero passages are only counted during the inspiration phase so that the control only reacts in the case of inspiratory snoring. The variance of the actual pressure can also be used for detecting snoring.

According to the teaching of DE 101 18 968 a detector for the cessation of breathing, an apnea detector, a hypopnea detector and a respiratory flow limitation detector are calculated from the features as an indication of an increase in pressure, and a normal detector as an indication of stable breathing and possible pressure reduction. The responses of the detector for the cessation of breathing, of the apnea detector, hypopnea detector and respiratory flow limitation detector are particularly designated as respiratory events in the text below.

The detector for the cessation of breathing will respond if more than two minutes have lapsed without detection of a breath. If this happens more than three times, the automatic pressure regulation will stop.

The apnea detector first determines respirations in which the expiration time is longer than 10 s and which are designated as breathing cessations. The apnea detector will respond if either in two successive cessations of breathing one of the cessations lasts for more than 30 s or if there are more than three successive cessations of breathing. Cessations of breathing are successive if the duration of the intermediate hyperventilation block and breathing period is <60 s.

The non-standardized mean inspiration volume, the reverse correlation and the snoring feature are used for hypopnea detection. The snoring feature, the mean curvature and the reverse correlation are used for detecting respiratory flow limitation. As for details of the hypopnea detector and the respiratory flow limitation detector, reference is made to DE 101 18 968.

The normal detector uses the correlation feature for detecting stable breathing. Stable breathing is present when the desired pressure has not been changed for a predetermined period, e.g. 180 s, and when the reverse correlation is e.g. $\geq 0.86$ during this period.

The fuzzy logic is also known in the prior art. According to conventional logic, logic variables can just assume the states 0 and 1, also designated as "false" and "true". In fuzzy logic, the fuzzy variables can assume any desired value between 0 and 1, including 0 and 1. The fuzzy logic is above all used in controls which are to take into account the experts' experience.

According to the fuzzy logic, fuzzy variables indicate membership in a set. In a fuzzy control the set corresponds to a specific operative state of the device to be controlled. With the help of the fuzzy logic it is possible to design a control in consideration of a limited number of typical operative states. The fuzzy logic supplies a formalism for the interpolation between the states considered.

It is desirable to provide a method for controlling the pressure of a CPAP device, a CPAP device for carrying out the method, and a storage medium for a corresponding program, which determine a CPAP pressure which is optimum for the patient, on the basis of the time dependence of a patient's respiratory flow curve.

SUMMARY OF THE INVENTION

According to an embodiment of the invention, a method for controlling the pressure supplied by a CPAP device is provided. The method comprises repeatedly measuring a respiratory flow during operation of the CPAP device. At least one respiratory event from the measured time-dependent behavior of the respiratory flow is determined. A respiratory event represents an indication that the pressure supplied by the CPAP device is too low. As long as no respiratory event is detected, the pressure supplied by the CPAP device is slowly, quasi ramp-like lowered.

According to another embodiment of the invention, a device for carrying out the CPAP therapy is provided. The device comprises an instruction memory storing instructions, a central processing unit for executing the instructions stored in the instruction memory, and a flow sensor electrically connected to the central processing unit for repeatedly measuring a respiratory flow during operation of the device under control of the central processing unit. The instructions make the central processing unit determine at least one respiratory event from the time-dependent behavior of the respiratory flow. A respiratory event represents an indication that the pressure supplied by the CPAP device is too low. As long as no respiratory event is detected, the pressure supplied by the CPAP device is slowly, quasi ramp-like lowered.

According to a further embodiment of the invention a storage medium for use with a CPAP device is provided. The CPAP device comprises a central processing unit for executing instructions stored in the storage medium and a flow sensor electrically connected to the central processing unit for measuring a respiratory flow. The instructions making the central processing unit and the flow sensor repeatedly measure a respiratory flow during operation of the CPAP device. At least one respiratory event is determined from the time-dependent behavior of the respiratory flow. A respiratory event represents an indication that the pressure supplied by the CPAP device is too low. As long as no respiratory event is detected, the pressure supplied by the CPAP device is slowly, quasi ramp-like lowered.

A slow reduction of the pressure supplied by the CPAP device has the advantage that the pressure can be adjusted much more finely than in the 1 mbar steps indicated in DE 101 18 968. The adjusted pressure will be more optimal i.e., it is better to keep the condition as minimal as possible, but to satisfy it as much as needed.

An increase in the absolute value of the pressure variation rate in time has the advantage that the pressure supplied by the CPAP device is lowered rapidly if it is still far beyond the optimum pressure.

The occurrence of a respiratory event indicates that the pressure supplied by the CPAP device is already slightly too low. Under these circumstances it is advantageous to raise the pressure by a predetermined value in a quick way, i.e. in steps if possible.

When the CPAP device has approximately reached the optimum pressure, it decreases the set pressure so to speak by way of trial in a ramp-like manner to provoke a respiratory event. If after the step-like raising of the pressure the pressure at the beginning of the ramp is approximately reached, this is an indication that the optimum pressure has approximately been reached. Under these circumstances it is advantageous to subject the patient less frequently to a trial-like reduction and thus to extend the time for keeping the pressure constant.

The prevention of a ramp in the case of an excessively small reverse correlation is also helpful in an advantageous way in that the patient is not disturbed in his sleep by the trial-like provocation of a respiratory event by reducing the pressure supplied by the CPAP device.

BRIEF DESCRIPTION OF THE DRAWINGS

Preferred embodiments of the invention will hereinafter be explained in more detail with reference to the attached drawings, wherein.

Figure 2:
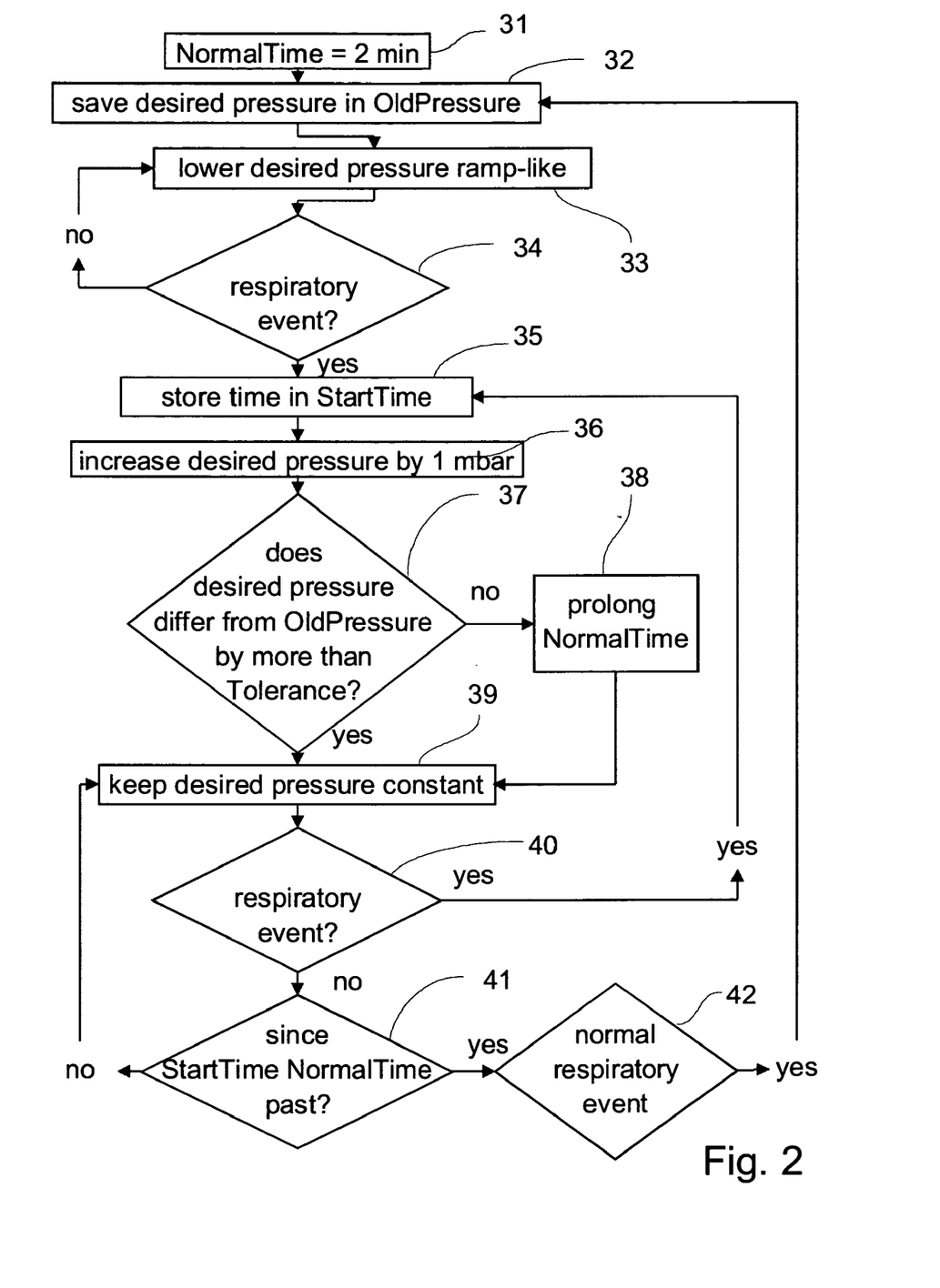
FIG. 2 shows a flow diagram for explaining the method according to the invention.

FIG. 2 explains the method of the invention by way of a flow diagram. The method is essentially based on the ramp-like reduction of the desired pressure in step 33.

DETAILED DESCRIPTION OF THE INVENTION

The invention is based on the finding that even with a slow change in the desired pressure the above-mentioned features, such as expiration time, particularly the reverse correlation, a mean inspiration volume and a mean curvature of the respiratory flow will change only insignificantly with time as long as the desired pressure is still above the optimum pressure, i.e. as long as no respiratory events occur. 1 mbar per breath can be taken as the upper limit value for the absolute value of the derivative of the pressure after time. The actually used rate should be low in comparison with this value, i.e. lower than 0.2 mbar per breath.

For initializing the method a value of two minutes is stored in step 31 in a memory with the name "NormalTime". Furthermore, the actual desired pressure is stored in step 32 in the memory "OldPressure". Subsequently, the desired pressure is reduced in step 33 in a ramp-like manner at a constant rate, i.e. the derivative of the desired pressure after time is constant. As has been mentioned above, the CPAP device is controlled by a microcontroller. Moreover, the signal supplied by the pressure sensor 11 is digitalized with a similar incrementation. The control of the turbine by the microcontroller is also carried out in fine digital increments. All of this has the effect that the desired pressure is actually not lowered in the form of a ramp, but rather in small increments. Therefore, a ramp-like lowering shall be understood for the purposes of this application when the pressure is lowered in a quasi ramp-like manner in several small increments with one respiratory cycle. A respiratory cycle lasts for about 4 to 5 s, so that a small increment is to take place after 1 s at the latest. The small increments should always be small in comparison with 1 mbar, i.e. smaller than 0.2 mbar.

In step 34, it is checked whether a respiratory event has occurred. A respiratory event is the opposite of a stable breathing, i.e. a respiratory disorder. In one embodiment, the detectors described in DE 101 18 968 can be used, except for the normal detector, i.e. especially the apnea, hypopnea and the respiratory flow limitation detector. In other embodiments, the latter may be used with further methods known from the prior art and used for detecting respiratory disorders, e.g. the admittance of respiratory flow as described in DE 691 32 030 T2, divided by pressure, or the reduced respiratory flow and snoring as mentioned in WO 99/24099.

As long as there is no respiratory event, the desired pressure is further lowered in step 33. If a respiratory event occurs in step 34, the actual time is stored in the memory "StartTime" in step 35 for further use in step 41.

Subsequently, the desired pressure is increased in step 36 by a predetermined value in steps, e.g. by 1 mbar. The actual pressure follows the desired pressure according to the inertia of the turbine 8 and the selected control parameters for the control of the actual pressure towards the desired pressure. A step-like increase in the actual pressure supplied by the CPAP device is here to mean a rise which takes place within one respiratory cycle, i.e. within 4 to 5 s. The reason for the step-like raising of the desired pressure as rapidly as possible is that upon occurrence of a respiratory event the actual pressure is already too low for the actual sleeping state of the patient. The excessively low pressure should be raised as fast as possible so that the patient's sleep is not disturbed by further respiratory events.

After the desired pressure has been raised in step 36, the desired pressure is compared with the value stored in the memory "OldPressure". In the memory "OldPressure", the desired pressure was stored in step 32 at the beginning of the ramp. When the desired pressure differs from the pressure stored in the memory "OldPressure" by more than the tolerance in step 37, this is interpreted as an indication that the pressure at the beginning of the ramp was positioned near the optimum pressure for the actual sleeping state of the patient. In this case the time stored in the memory "NormalTime" is prolonged in step 38 so that the patient's sleep is not unnecessarily disturbed by further respiratory events that are provoked by way of trial by reducing the desired pressure in step 33. The prolongation in step 38 can take place by addition of a constant value or by multiplication with a value greater than 1.

Following step 37 or 38, the desired pressure is kept constant at least for the time stored in the memory "NormalTime". This condition is checked in step 41. While the desired pressure is being kept constant, it is further checked in step 40 whether respiratory events occur. If this is the case, the desired pressure is further raised in step 36 after the actual time has been stored in the memory "StartTime" in step 35.

After it has been determined in step 41 that since the time stored in memory "StartTime" the time stored in the memory "NormalTime" has lapsed, it is checked in step 42 whether the normal detector has reacted. As has been explained above, the reverse correlation can be evaluated for this purpose. Hence, there is a normal event when the reverse correlation is greater than a predetermined value, for instance 0.86. Whenever the breathing already starts to get irregular, i.e. when the reverse correlation falls below the predetermined threshold value, it is thus omitted that a respiratory event is provoked in step 34 by further reduction of the desired pressure. Another normal detector is described U.S. Pat. application Ser. No. 11/132.695.

This leads in an advantageous way to a more restful and relaxing sleep. If the reverse correlation is sufficiently high, i.e. if a normal event is determined in step 42, one starts again to lower the desired pressure in step 33 after the actual desired pressure has been stored in the memory "OldPressure" in step 32 until a respiratory event is determined in step 34.

Figure 3:
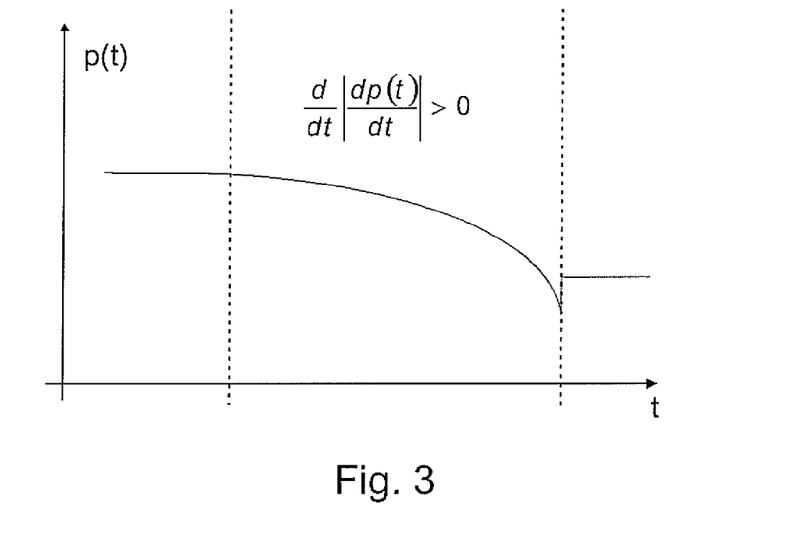
FIG. 3 graphically illustrates the desired pressure over time in accordance with one embodiment of the invention.

In another embodiment, the desired pressure is not lowered in step 33 with a ramp at a constant rate, but at a rate rising in its absolute value with time. This has the effect that the desired pressure approaches the optimum pressure within less time when the desired pressure is still far above the optimum pressure at the beginning. For instance, the rate can be raised in proportion to the time that has lapsed since the beginning of the ramp, so that a downwardly opened parabola is obtained for the desired pressure (see. e.g.. F*ig.* 3).

In a further embodiment, the events detected by the detectors are treated as fuzzy variables. An advantage of this embodiment is that the control operates continuously. Preferably, the transition from "no event" to "event has occurred", i.e. the range in which the fuzzy variable rises from 0 to 1, is such that the corresponding fuzzy variable reaches the value 0.5 in the case of the above-indicated limit value. Hence, in consideration of the gradual transition from 0 to 1 of fuzzy variables, it can be said that e.g. a normal event is detected or recognized all the more the more clearly the reverse correlation exceeds the threshold value of e.g. 0.86.

The width of the chosen transition range and the extension of the transition function are of minor importance to the quality of the control method. Thus, the normal fuzzy variable can e.g. assume the value zero when the reverse correlation is smaller than 0.82, it can rise linearly from 0 to 1 when the reverse correlation falls within the range between 0.82 and 0.9, and it can be 1 when the reverse correlation exceeds the value 0.9. However, other functions, such as a suitably scaled arctan function or a probability integral $\Phi(x)$, may be used for the design of the transition range:

$$\Phi(x) = \frac{1}{\sqrt{2\pi}} \int_{-\infty}^{x} \exp\left(-\frac{z^2}{2}\right) dz \tag{1}$$

When fuzzy variables are used, the rate of the change in pressure is determined from the sum of the fuzzy variables supplied by the individual detectors and preferably weighted with coefficients. It is taken into account in the coefficients that e.g. upon detection of a cessation of breathing the pressure is raised rapidly while in the case of a respiratory flow limitation the desired pressure of the CPAP device is raised at a slower pace. Consequently, the coefficient for the fuzzy variable in the case of a cessation of breathing is greater than that for the fuzzy variable in the case of respiratory flow limitation.

In one fuzzy embodiment of the invention, the absolute value of the rate at which the desired pressure is lowered in step 33 can be reduced when one or more respiratory events are already recognized to a slight degree, i.e. the fuzzy variables have values in the range of 0.1 or 0.2. The desired pressure is thereby reduced at a slower pace when breathing is less regular.

The step height of the increase in the desired pressure in step 36 can also be made dependent on the fuzzy variable with which the respiratory event has occurred. In one embodiment, one respective fuzzy variable has occurred for a specific respiratory event, such as apnea or hypopnea. In one embodiment, the increase in the desired pressure depends on the fuzzy variable with the highest value, i.e. the fuzzy variable that is the most likely one to signalize a respiratory event. For instance, if this variable has a value of 0.8, the desired pressure is raised by 1 mbar. If it has a value of 0.9, the increase in the desired pressure may be 1.1 mbar.

For instance, it is also possible to start the lowering of the desired pressure at a very slow rate when the reverse correlation approaches the value of 0.86 from below so that the corresponding fuzzy variable announces a normal event more and more clearly. In another embodiment, the lowering of the desired pressure can also be started at a low rate when the time stored in the memory "NormalTime" has not fully lapsed yet.

The above-described desired-pressure control methods according to the invention can also be used in BiPAP device and in multilevel device. The desired pressure determined according to the control method can here be used as the higher pressure in BiPAP device or as the highest pressure in multilevel device. In another embodiment, the pressure determined according to a control method of the invention indicates the mean value in time of the pressures generated by a BiPAP or multilevel device.

A CPAP device may be equipped with a slot 6 which is connected via a data line 10 to the microcontroller 5. A storage medium 7 may be inserted into the slot 6 to store another program in the microcontroller 5. The firmware can thereby be updated.

In the foregoing, the invention was explained in more detail by means of preferred embodiments. For a person skilled in the art it is obvious, however, that different alterations and modifications may be made, without departing from the spirit of the invention. Therefore, the scope of protection is defined by the following claims and the equivalents thereof.

| List of Reference Numerals | |
|---|---|
| 1 | CPAP device |
| 2 | Hole |
| 4 | Compressor |
| 5 | Microcontroller |
| 6 | Slot |
| 7 | Storage medium |
| 8 | Turbine |
| 9 | Respiration tube |
| 10 | Data line |
| 11 | Pressure sensor |
| 16 | Flow sensor |
| 17 | Heating wire |
| 18 | Respiration mask |
| 19 | Sleeping person |
| 31-42 | Steps |

What is claimed is:

1. A method for controlling the pressure supplied by a CPAP device, comprising:
   repeatedly measuring of a respiratory flow during operation of the CPAP device;
   determining at least one respiratory event from the measured time-dependent behavior of the respiratory flow, a respiratory event representing an indication that the pressure supplied by the CPAP device is too low; and
   slow, quasi ramp-like lowering of the pressure supplied by the CPAP device as long as no respiratory event is detected, an absolute value of a time derivative of the pressure supplied by the CPAP device rising during the slow, quasi ramp-like lowering.

2. The method according to claim 1, further comprising raising the pressure supplied by the CPAP device upon occurrence of a respiratory event.

3. A method for controlling the pressure supplied by a CPAP device, comprising:
   repeatedly measuring a respiratory flow during operation of the CPAP device;
   determining at least one respiratory event from a measured time-dependent behavior of the respiratory flow, the respiratory event representing an indication that the pressure supplied by the CPAP device is too low;
   slow, quasi ramp-like lowering of the pressure supplied by the CPAP device as long as no respiratory event is detected;
   raising the pressure supplied by the CPAP device to a new pressure in one step by a predetermined value upon occurrence of a respiratory event; and
   keeping constant the new pressure supplied by the CPAP device for a predetermined time after the respiratory event;
   starting the slow, quasi-continuous lowering of the pressure supplied by the CPAP device when no respiratory event has been detected for the predetermined time;
   comparing the pressure supplied by the CPAP device after raising by the predetermined value with the pressure at the beginning of the raising of the preceding slow, quasi ramp-like lowering of the pressure supplied by the CPAP device to obtain a pressure difference;
   comparing an absolute value of the pressure difference with a threshold value; and
   extending the predetermined time if the absolute value of the pressure difference is lower than the threshold value.

4. The method according to claim 1, further comprising:
   determining the most recent respiratory cycle;
   calculating a correlation value between the most recent respiratory cycle and said preceding respiratory cycles;
   averaging over the correlation values;
   determining whether the mean value is above a predetermined threshold value; and
   starting with the slow, quasi-continuous lowering of the pressure supplied by the CPAP device only if the threshold value is not exceeded.

5. The method according to claim 3, the method terminating the keeping constant of the pressure supplied by the CPAP device and raises the pressure if a respiratory event is detected.

6. A device for carrying out the CPAP therapy comprising:
   an instruction memory for storing instructions;
   a central processing unit for executing the instructions stored in the instruction memory;
   a flow sensor electrically connected to the central processing unit for repeatedly measuring a respiratory flow during operation of the device under control of the central processing unit;
   the instructions making the central processing unit perform the following, when being executed:
   determining at least one respiratory event from the time-dependent behavior of the respiratory flow, a respiratory event representing an indication that the pressure supplied by the CPAP device is too low; and
   slowly, quasi ramp-like lowering the pressure supplied by the CPAP device as long as no respiratory event is detected, an absolute value of a time derivative of the pressure supplied by the CPAP device rising during the slow, quasi ramp-like lowering.

7. The device according to claim 6, the central processing unit further raising the pressure supplied by the CPAP device upon occurrence of a respiratory event.

8. A device for carrying out the CPAP therapy comprising:
   an instruction memory for storing instructions;
   a central processing unit for executing the instructions stored in the instruction memory;
   a flow sensor electrically connected to the central processing unit for repeatedly measuring a respiratory flow during operation of the device under control of the central processing unit;
   the instructions making the central processing unit perform the following, when being executed:
   determining at least one respiratory event from the time-dependent behavior of the respiratory flow, a respiratory event representing an indication that the pressure supplied by the CPAP device is too low;
   slowly, quasi ramp-like lowering the pressure supplied by the CPAP device as long as no respiratory extent is detected;
   raising the pressure supplied by the CPAP device to a new pressure in one step by a predetermined value upon occurrence of a respiratory event; and
   keeping constant the pressure supplied by the CPAP device for a predetermined time after the respiratory event;
   starting the slow, quasi-continuous lowering of the pressure supplied by the CPAP device when no respiratory event has been detected for the predetermined time;
   comparing the pressure supplied by the CPAP device after raising by the predetermined value with the pressure at the beginning of the raising of the preceding slow, quasi ramp-like lowering of the pressure supplied by the CPAP device to obtain a pressure difference;
   comparing an absolute value of the pressure difference with a threshold value; and
   extending the predetermined time if the absolute value of the pressure difference is lower than the threshold value.

9. The device according to claim 6, the central processing unit further performing:
   determining the most recent respiratory cycle;
   calculating a correlation value between the most recent respiratory cycle and said preceding respiratory cycles;
   averaging over the correlation values;
   determining whether the mean value is above a predetermined threshold value; and
   starting with the slow, quasi-continuous lowering of the pressure supplied by the CPAP device only if the threshold value is not exceeded.

10. The device according to claim 8, the central processing unit terminating the keeping constant of the pressure supplied by the CPAP device and raising the pressure if the central processing unit detects a respiratory event while the pressure has been kept constant.

11. A storage medium for use with a CPAP device; the CPAP device comprising a central processing unit for executing instructions stored in the storage medium and a flow sensor electrically connected to the central processing unit for measuring a respiratory flow; the instructions making the central processing unit perform the following when being executed:

repeatedly measuring a respiratory flow during operation of the CPAP device by the flow sensor;

determining at least one respiratory event from the time-dependent behavior of the respiratory flow, a respiratory event representing an indication that the pressure supplied by the CPAP device is too low; and slowly, quasi ramp-like lowering the pressure supplied by the CPAP device as long as no respiratory event is detected, an absolute value of a time derivative of the pressure supplied by the CPAP device rising during the slow, quasi ramp-like lowering.

12. A storage medium for use with a CPAP device, the CPAP device comprising a central processing unit for executing instructions stored in the storage medium and a flow sensor electrically connected to the central processing unit for measuring a respiratory flow; the instructions making the central processing unit perform the following when being executed:

repeatedly measuring a respiratory flow during operation of the CPAP device by the flow sensor;

determining at least one respiratory event from the time-dependent behavior of the respiratory flow, a respiratory event representing an indication that the pressure supplied by the CPAP device is too low; and slowly, quasi ramp-like lowering the pressure supplied by the CPAP device as long as no respiratory event is detected;

raising the pressure supplied by the CPAP device to a new pressure in one step by a predetermined value upon occurrence of a respiratory event; and keeping constant the pressure supplied by the CPAP device for a predetermined time after the respiratory event;

starting the slow, quasi-continuous lowering of the pressure supplied by the CPAP device when no respiratory event has been detected for the predetermined time;

comparing the pressure supplied by the CPAP device after raising by the predetermined value with the pressure at the beginning of the raising of the preceding slow, quasi ramp-like lowering of the pressure supplied by the CPAP device to obtain a pressure difference;

comparing an absolute value of said pressure difference with a threshold value; and extending the predetermined time if the absolute value of the pressure difference is lower than the threshold value.

13. The method according to claim 3, further comprising:

determining the most recent respiratory cycle;

calculating a correlation value between the most recent respiratory cycle and said preceding respiratory cycles;

averaging over the correlation values;

determining whether the mean value is above a predetermined threshold value; and starting with the slow, quasi-continuous lowering of the pressure supplied by the CPAP device only if the threshold value is not exceeded.

14. The device according to claim 8, the central processing unit further performing:

determining the most recent respiratory cycle;

calculating a correlation value between the most recent respiratory cycle and said preceding respiratory cycles;

averaging over the correlation values;

determining whether the mean value is above a predetermined threshold value; and starting with the slow, quasi-continuous lowering of the pressure supplied by the CPAP device only if the threshold value is not exceeded.

* * * * *

UNITED STATES PATENT AND TRADEMARK OFFICE
CERTIFICATE OF CORRECTION

PATENT NO. : 7,661,426 B2 Page 1 of 1
APPLICATION NO. : 11/132462
DATED : February 16, 2010
INVENTOR(S) : Lauk et al.

It is certified that error appears in the above-identified patent and that said Letters Patent is hereby corrected as shown below:

Claim 8, column 10, line 34, please replace "extent" with -- event --.

Signed and Sealed this

First Day of June, 2010

David J. Kappos
*Director of the United States Patent and Trademark Office*